United States Patent
Savord et al.

(10) Patent No.: US 8,169,125 B2
(45) Date of Patent: May 1, 2012

(54) TRANSDUCER ARRAYS FOR MEDICAL ULTRASOUND AND METHOD OF MAKING THE SAME

(75) Inventors: Bernard J. Savord, Andover, MA (US); Martha Grewe Wilson, Andover, MA (US); Wojtek Sudol, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 840 days.

(21) Appl. No.: 11/573,792

(22) PCT Filed: Aug. 15, 2005

(86) PCT No.: PCT/IB2005/052687
§ 371 (c)(1),
(2), (4) Date: Sep. 18, 2008

(87) PCT Pub. No.: WO2006/018806
PCT Pub. Date: Feb. 23, 2006

(65) Prior Publication Data
US 2009/0105596 A1 Apr. 23, 2009

(51) Int. Cl.
*H01L 41/09* (2006.01)
(52) U.S. Cl. ........................ 310/334; 310/311
(58) Field of Classification Search .......... 310/334, 310/311, 313 B, 331, 327; 600/437, 459; H01L 41/08, 41/09
See application file for complete search history.

(56) References Cited

U.S. PATENT DOCUMENTS

| 6,589,180 | B2* | 7/2003 | Erikson et al. | 600/459 |
| 2003/0013969 | A1 | 1/2003 | Erikson | |
| 2007/0276238 | A1* | 11/2007 | Sudol | 310/311 |
| 2008/0106976 | A1* | 5/2008 | Davidsen et al. | 367/140 |
| 2010/0156243 | A1* | 6/2010 | Weekamp et al. | 310/334 |

OTHER PUBLICATIONS

"A 128×128 Ultrasonic Transducer Hybrid Array", by K. Erikson et al., Untrasonics Symposium, 1997 IEEE, vol. 2.

* cited by examiner

*Primary Examiner* — Thomas Dougherty
*Assistant Examiner* — Karen B Addison
(74) *Attorney, Agent, or Firm* — W. Brinton Yorks, Jr.

(57) ABSTRACT

An ultrasound transducer (40,70,100) comprises a combined individual die integrated circuit (42,72,102) and an array of acoustic elements (44,74,104) coupled to the combined individual die integrated circuit via an array of flip-chip bumps (46,76,106). The combined individual die integrated circuit includes a first integrated circuit die (48,78,108) aligned with at least one additional integrated circuit die (50,80,(110,112)). In addition, the first integrated circuit die, the at least one additional die integrated circuits, and the array of acoustic elements together form a large aperture transducer array.

15 Claims, 8 Drawing Sheets

TRANSDUCER ARRAYS FOR MEDICAL ULTRASOUND AND METHOD OF MAKING THE SAME

This application relates to the application Ser. No. 11/573,753, entitled "Ultrasound Transducer and Method For Implementing High Aspect Ratio Bumps for Flip-Chip Two-Dimensional Arrays", Wojtek Sudol, filed concurrently herewith and incorporated herein by reference in its entirety.

The present disclosure generally relates to transducer arrays for use in medical ultrasound, and more particularly, to a method and apparatus for implementing flip-chip two-dimensional arrays.

In medical ultrasound, two-dimensional transducer arrays are generally used for transmission and reception of ultrasonic or acoustic waves during ultrasound diagnostic imaging. State of the art two-dimensional arrays generally include a flat array having on the order of about three thousand (3,000) transducer elements. In one type of ultrasound transducer design, all transducer elements of an array are attached and individually electrically connected to a surface of an integrated circuit (IC) via flip-chip technology using conductive bumps. The IC provides electrical control of the elements, such as, for beam forming, signal amplifying, etc.

One example of a typical design of an ultrasound transducer is illustrated in FIG. 1. The ultrasound transducer 10 includes a flat array of acoustic elements 12 that are coupled to a surface of an integrated circuit 14 via flip-chip conductive bumps 16. A flip-chip underfill material 18 is included within a region between the flip-chip conductive bumps 16, the integrated circuit 14 and the flat array of acoustic elements 12. Transducer 10 further includes a transducer base 20 and an interconnection cable 22. Interconnection cable 22 is for interconnecting between the integrated circuit 14 and an external cable (not shown). Integrated circuit 14 is electrically coupled to the interconnection cable 22 via wirebonded wires 24, using techniques known in the art.

FIG. 2 is a top plan view of an integrated circuit chip 14 used in the conventional ultrasound transducer 10 of FIG. 1. The integrated circuit chip 14 includes an array of flip-chip connections 16 disposed in a center of the chip, the array 16 comprising on the order of 2500-3000 connections. In addition, the integrated circuit chip 14 includes first and second plurality of IC-to-flex connections (26 and 28, respectively) disposed on respective first and second side edges (27 and 29, respectively) of the chip 14. Each of the first and second plurality of IC to flex connections can include on the order of 100 connections.

Flip-chip assembly is a technique that allows attachment of a bare integrated circuit (IC) chip directly to a substrate in a face-down configuration. An IC chip can also be referred to as a die. With flip-chip assembly, the electrical connections between the IC chip and the substrate is achieved via conductive "bumps". The height of the conductive bumps defines the distance between the IC chip and the substrate. Accordingly, flip-chip technology offers many advantages, including for example high density I/O count and short interconnect distance.

Integrated circuit and flip-chip technology can be applied to a large percentage of ultrasound transducer applications but it also has a great limitation. That is, the IC fabrication technology is limited to small size parts, and thus limits application of the IC technology to small transducer arrays. In addition, there presently exists a large application base for larger transducer arrays. However, the application base can not readily be addressed with the current integrated circuit and flip-chip technology.

Fabricating large size integrated circuits is a challenge. That is, fabrication of large size integrated circuits is limited by the size of a reticle used in the fabrication process. In other words, the circuitry of the entire IC must fit within the size of the reticle. Typical size of a reticle in under 2 cm×2 cm.

Accordingly, an improved ultrasound transducer and method of making the same for overcoming the problems in the art is desired.

According to one embodiment of the present disclosure, an ultrasound transducer comprises a combined individual die integrated circuit and an array of acoustic elements coupled to the combined individual die integrated circuit via an array of flip-chip bumps. The combined individual die integrated circuit includes a first integrated circuit die aligned with at least one additional integrated circuit die. In addition, the first integrated circuit die, the at least one additional integrated circuit die, and the array of acoustic elements together form a large aperture transducer array. Furthermore, the large aperture transducer array can include a 1D, 1.5D, or 2D transducer array.

In the figures, like reference numerals refer to like elements. In addition, it is to be noted that the figures are not drawn to scale.

In the manufacture of integrated circuits, a semiconductor wafer generally contains a number of integrated circuit die not yet separated into individual devices. Each of the integrated circuit die generally contains circuitry for performing desired functions according to the requirements of a particular integrated circuit application. For example, an integrated circuit could include ultrasound signal processing circuitry.

Furthermore, the ultrasound transducer application can include a cardiac application, an abdominal application, a transosophageal (TEE) application, or other diagnostic or therapeutic ultrasound application. Moreover, the shape of the transducer array can be flat, or it can be curved to form a curved linear array.

With respect to ultrasound devices, a simplified ultrasound transducer build process sequence could include the following steps. For example, the process begins with obtaining a wafer containing desired ultrasound transducer ICs, e.g., from an application specific integrated circuit (ASIC) vendor. A process of wafer bumping according to one of the embodiments of the present disclosure is performed on the wafer. Subsequent to wafer bumping, the wafer is thinned and separated into individual die, using standard techniques. A flip-chip operation is then performed. Following the flip-chip operation, a dicing operation provides separation of acoustic elements of an ultrasound transducer or sensor component. The sensor can then be attached to a frame, according to the requirements of the particular ultrasound transducer IC application.

Figure 1:
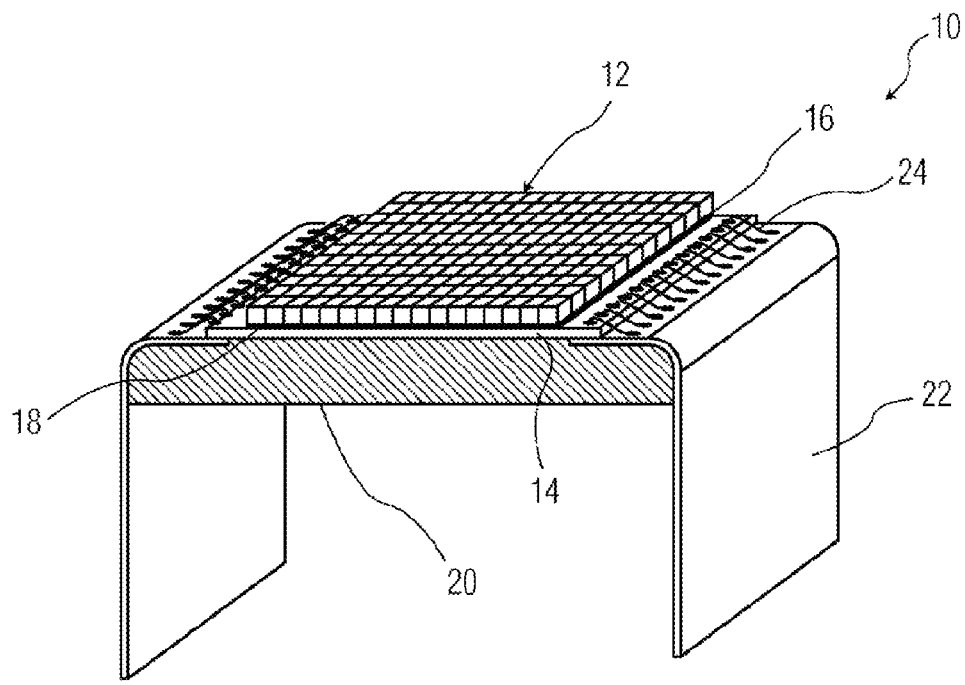
FIG. 1 is a plan view of a conventional ultrasound sensor.
Figure 2:
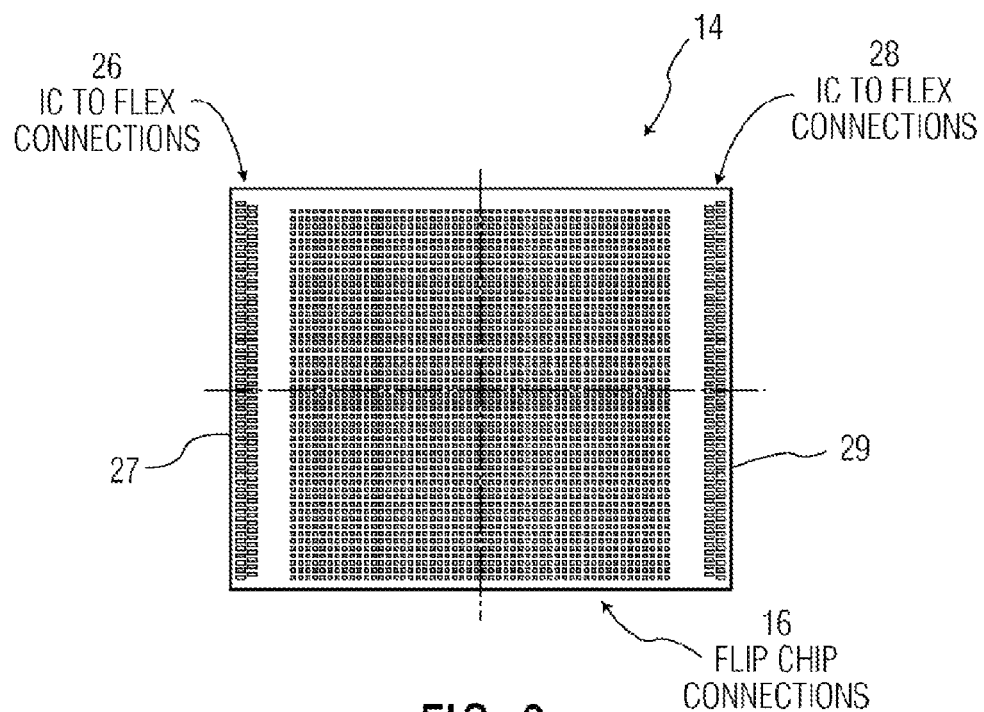
FIG. 2 is a top plan view of an integrated circuit chip used in the conventional ultrasound transducer of FIG. 1.
Figure 3:
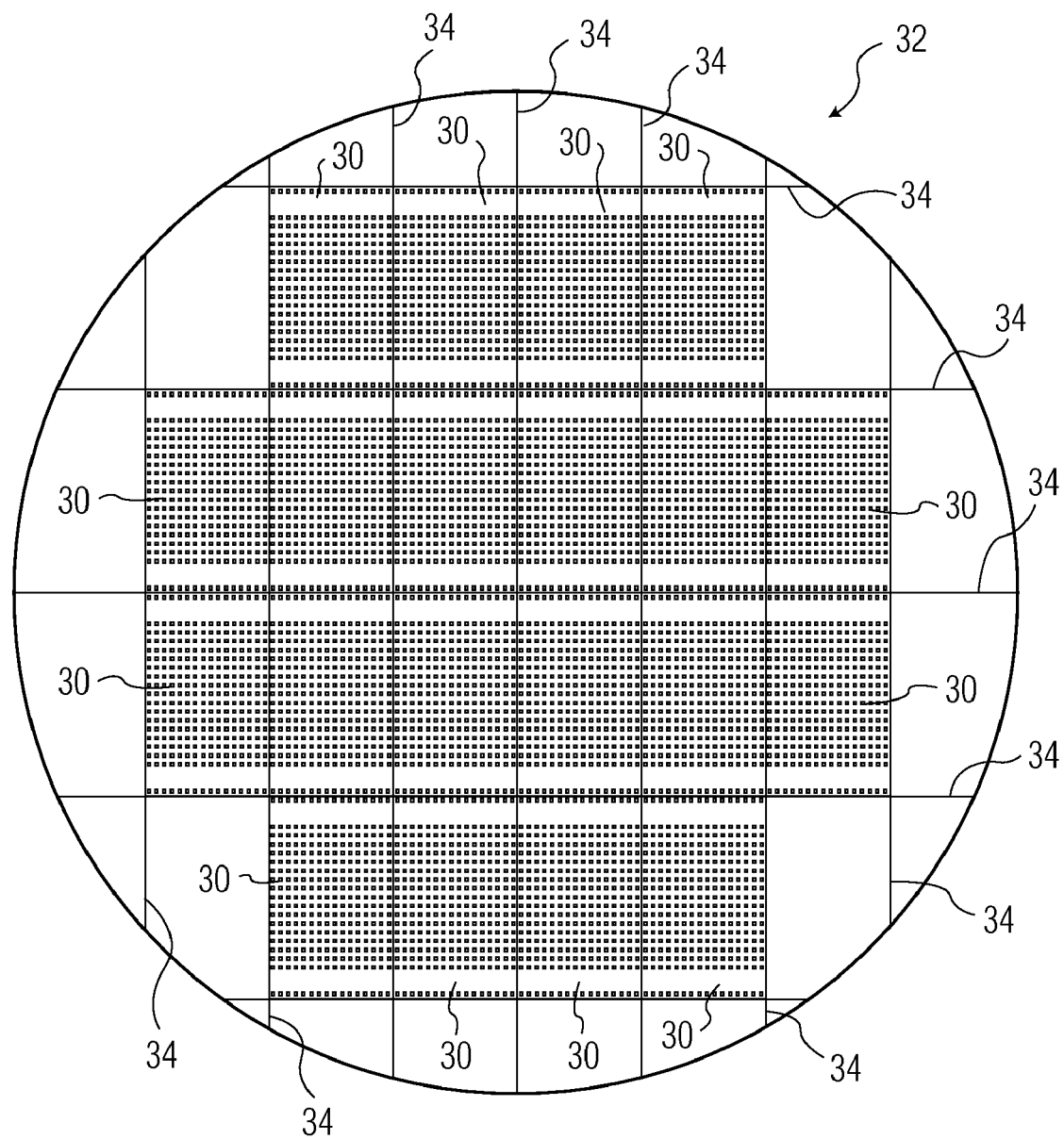
FIG. 3 is a top plan view of a plurality of integrated circuit chips on a wafer for use in making large aperture array two dimensional ultrasound transducers according to one embodiment of the present disclosure.
Figure 4:
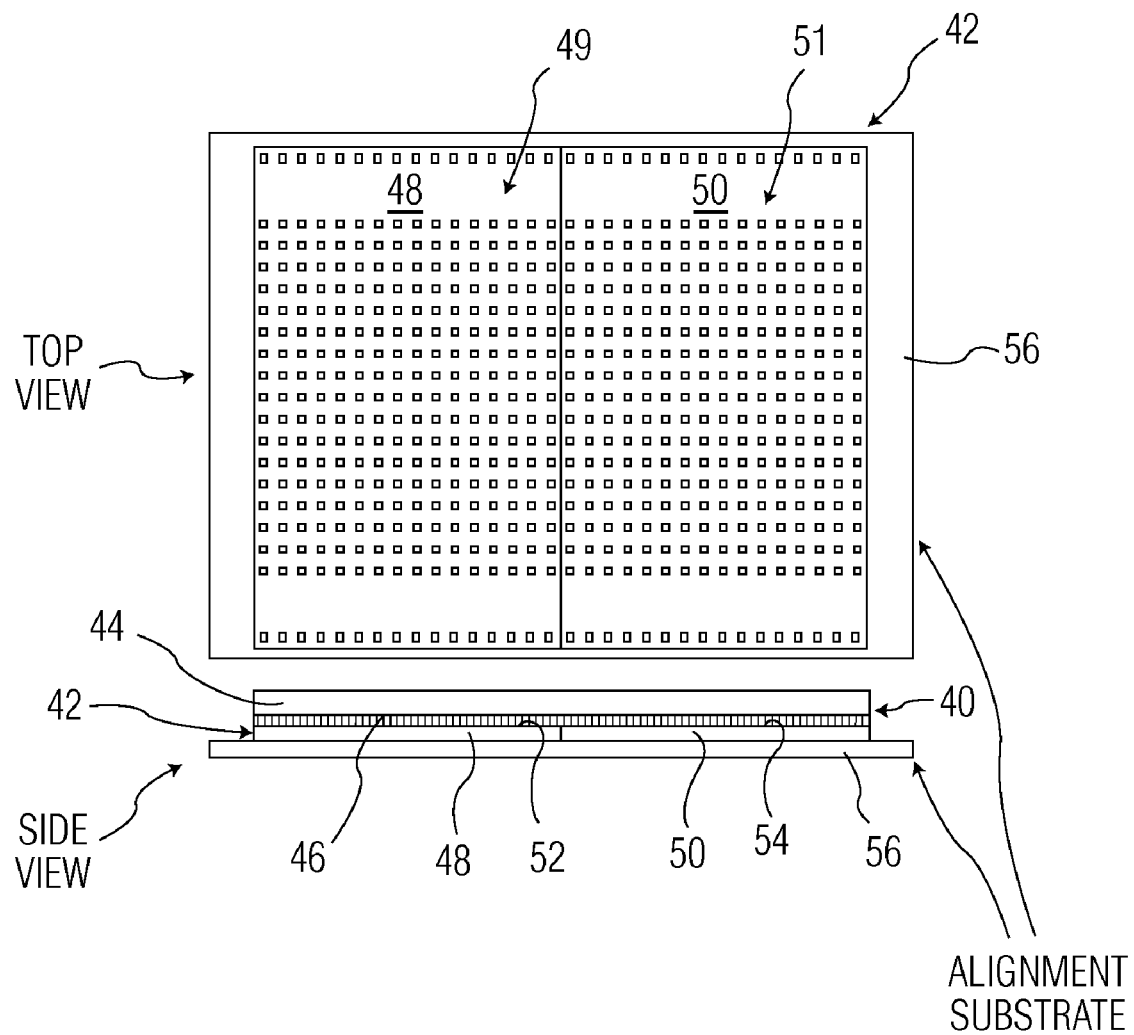
FIG. 4 is a top plan view of a portion of an ultrasound transducer in the formation of a large aperture array two dimensional ultrasound transducer using integrated circuits of FIG. 3 according to an embodiment of the present disclosure.

FIG. 3 is a top plan view of a plurality of integrated circuit chips 30 on a wafer 32 for use in making large aperture array two dimensional ultrasound transducers according to one embodiment of the present disclosure. Individual ones of the integrated circuit chips 30 of wafer 32 are singulated along dicing lines indicated by reference numeral 34. FIG. 4 is a top plan view of a portion of an ultrasound transducer 40 in the formation of a large aperture array two dimensional ultrasound transducer using integrated circuit chips 30 of FIG. 3 according to an embodiment of the present disclosure.

In one embodiment, an ultrasound transducer 40 comprises a combined individual die integrated circuit 42 and an array of acoustic elements (generally indicated by reference numeral 44) coupled to the combined individual die integrated circuit via an array of flip-chip bumps (generally indicated by reference numeral 46) and a suitable underfill material (not shown). The combined individual die integrated circuit 42 includes a first integrated circuit die 48 aligned with at least one additional integrated circuit die 50. In addition, the first integrated circuit die 48, the at least one additional integrated circuit die 50, and the array of acoustic elements 44 together form a large aperture two-dimensional transducer array 40.

In another embodiment, the first integrated circuit die 48 and the at least one additional integrated circuit die 50 each comprise an array of bond pads (generally indicated by reference numerals 49 and 51, respectively) on a flip-chip attachment surface 54 of a respective integrated circuit die. The bond pads have a pitch between adjacent bond pads. An alignment of the first integrated circuit die with the at least one additional integrated circuit die preserves a continuation of the pitch between bond pads on the respective first and at least one additional integrated circuit die.

The combined individual die integrated circuit 42 further includes the first integrated circuit die 48 and the at least one additional integrated circuit die 50 mounted on an alignment substrate 56. In one embodiment, the first integrated circuit die and the at least one additional integrated circuit die comprise two integrated circuit die. In another embodiment, the first integrated circuit die and the at least one additional integrated circuit die comprise three integrated circuit die. Furthermore, the first integrated circuit die and the at least one additional integrated circuit die may comprise two individual singulated integrated circuit die. In the later instance, the two individual singulated integrated circuit die are aligned with respect to one another and mounted on the alignment substrate.

Figure 5:
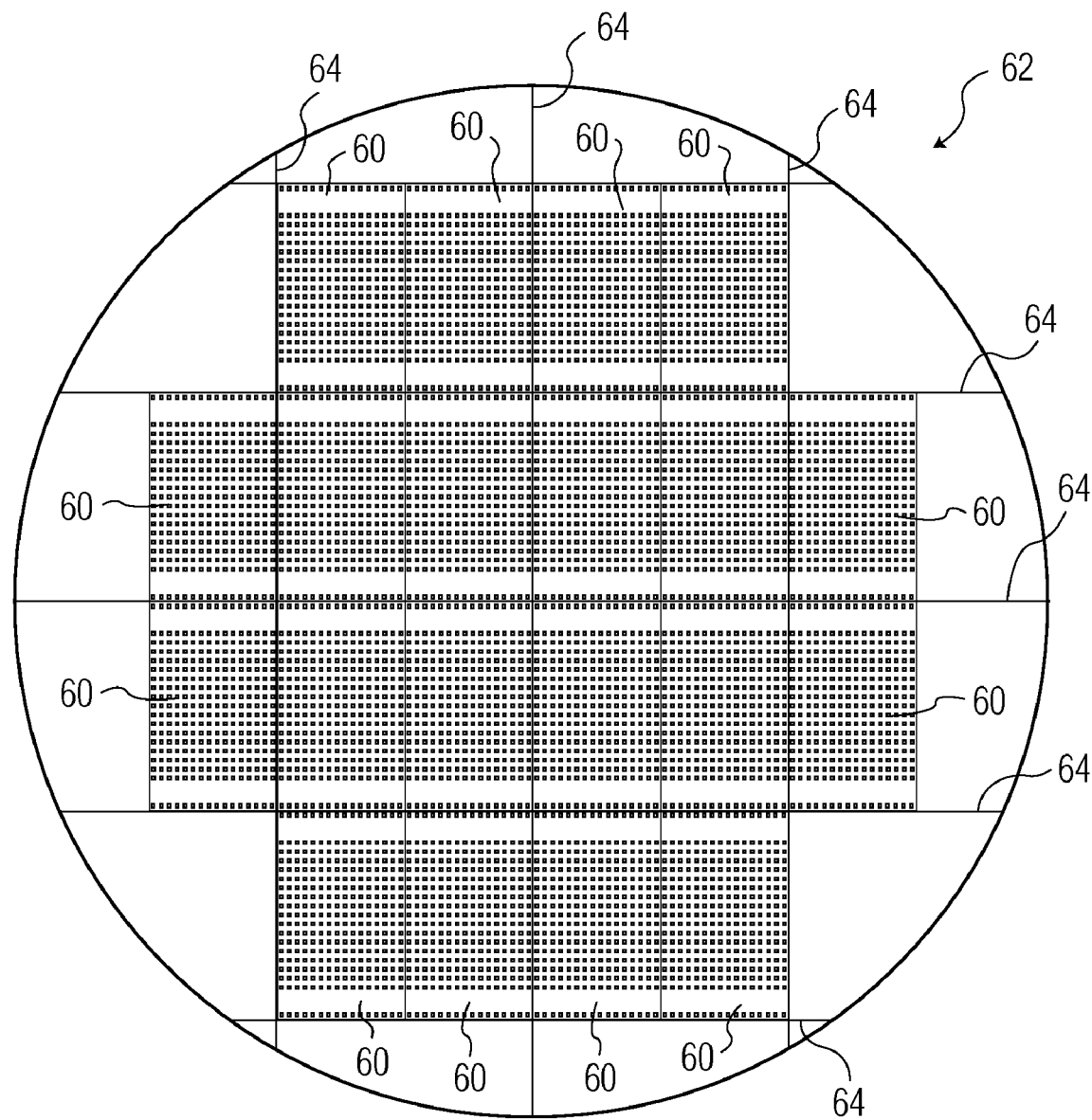
FIG. 5 is a top plan view of a plurality of integrated circuit chips on a wafer for use in making large aperture array two dimensional ultrasound transducers according to another embodiment of the present disclosure.
Figure 6:
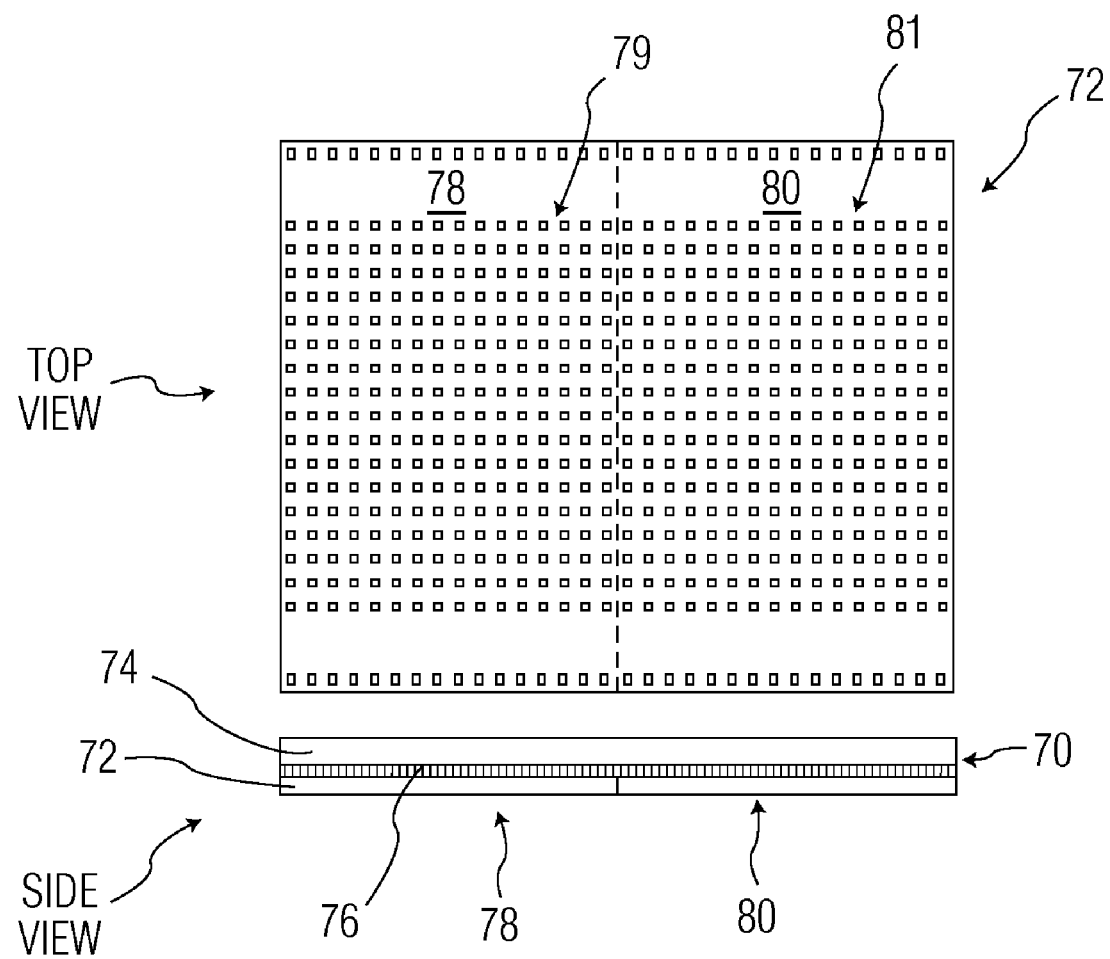
FIG. 6 is a top plan view of a portion of an ultrasound transducer in the formation of a large aperture array two dimensional ultrasound transducer using integrated circuits of FIG. 5 according to the another embodiment of the present disclosure.

FIG. 5 is a top plan view of a plurality of integrated circuit chips 60 on a wafer 62 for use in making large aperture array two dimensional ultrasound transducers according to another embodiment of the present disclosure. Desired ones of the integrated circuit chips 60 of wafer 62 are singulated along dicing lines indicated by reference numeral 64. FIG. 6 is a top plan view of a portion of an ultrasound transducer 70 in the formation of a large aperture array two dimensional ultrasound transducer using integrated circuits 60 of FIG. 5 according to the another embodiment of the present disclosure. The ultrasound transducer 70 comprises a combined individual die integrated circuit 72 and an array of acoustic elements (generally indicated by reference numeral 74) coupled to the combined individual die integrated circuit via an array of flip-chip bumps (generally indicated by reference numeral 76) and a suitable underfill material (not shown). The combined individual die integrated circuit 72 includes a first integrated circuit die 78 aligned with at least one additional integrated circuit die 80. That is, the first integrated circuit die 78 and the at least one additional integrated circuit die 80 comprise two individual integrated circuit die 60 aligned with respect to the other on a wafer 62. In such an instance, the two individual integrated circuit die 60 are singulated along dicing lines 64 together from the wafer 62 as the combined individual die integrated circuit 72. Furthermore, during a design portion of the particular ultrasound transducer application, individual die artwork on the wafer assures a continuation of an array pitch of the flip-chip bumps (generally indicated by reference numerals 79 and 81, respectively) between adjacent die.

Figure 7:
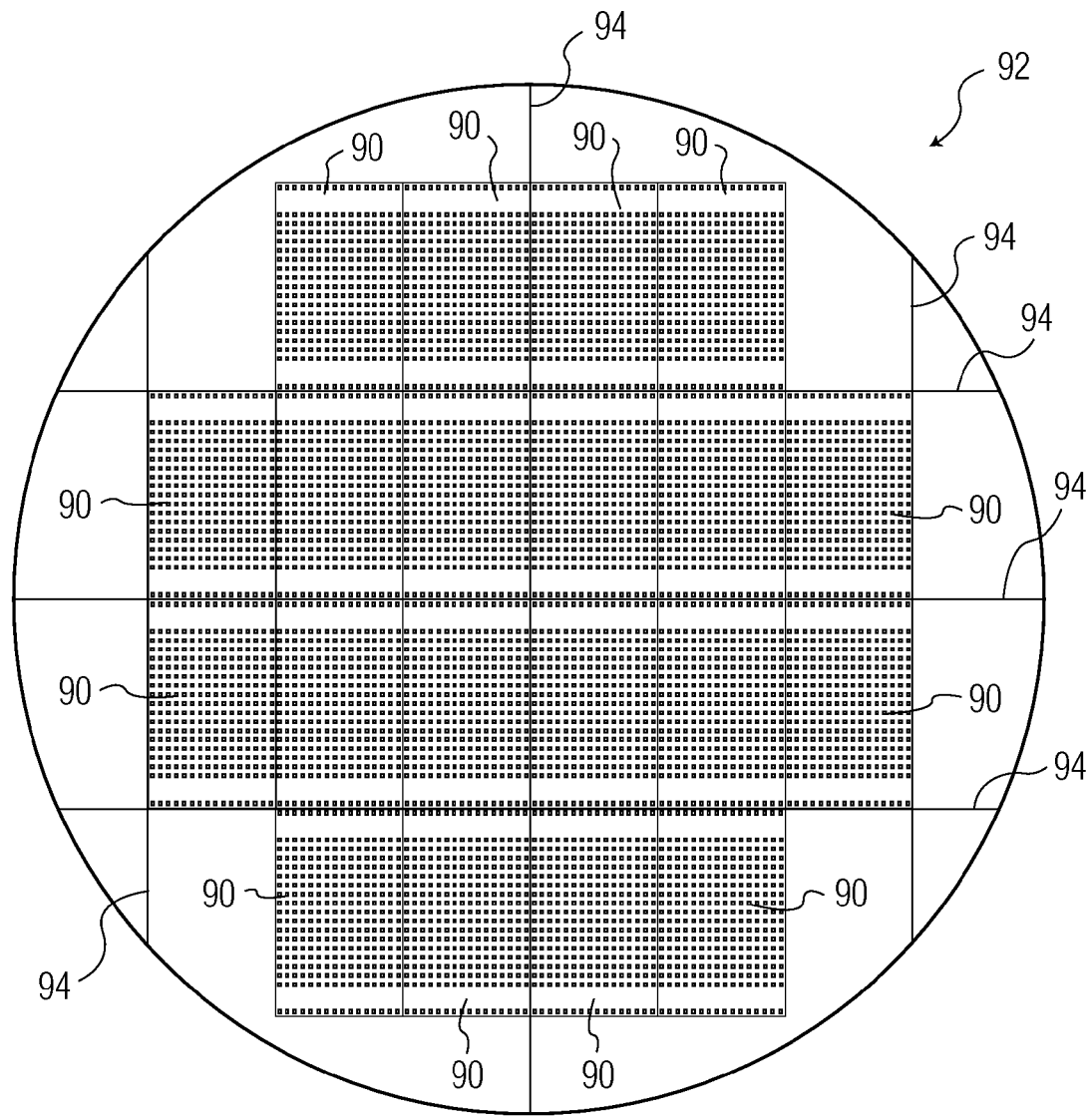
FIG. 7 is a top plan view of a plurality of integrated circuit chips on a wafer for use in making large aperture array two dimensional ultrasound transducers according to yet another embodiment of the present disclosure.
Figure 8:
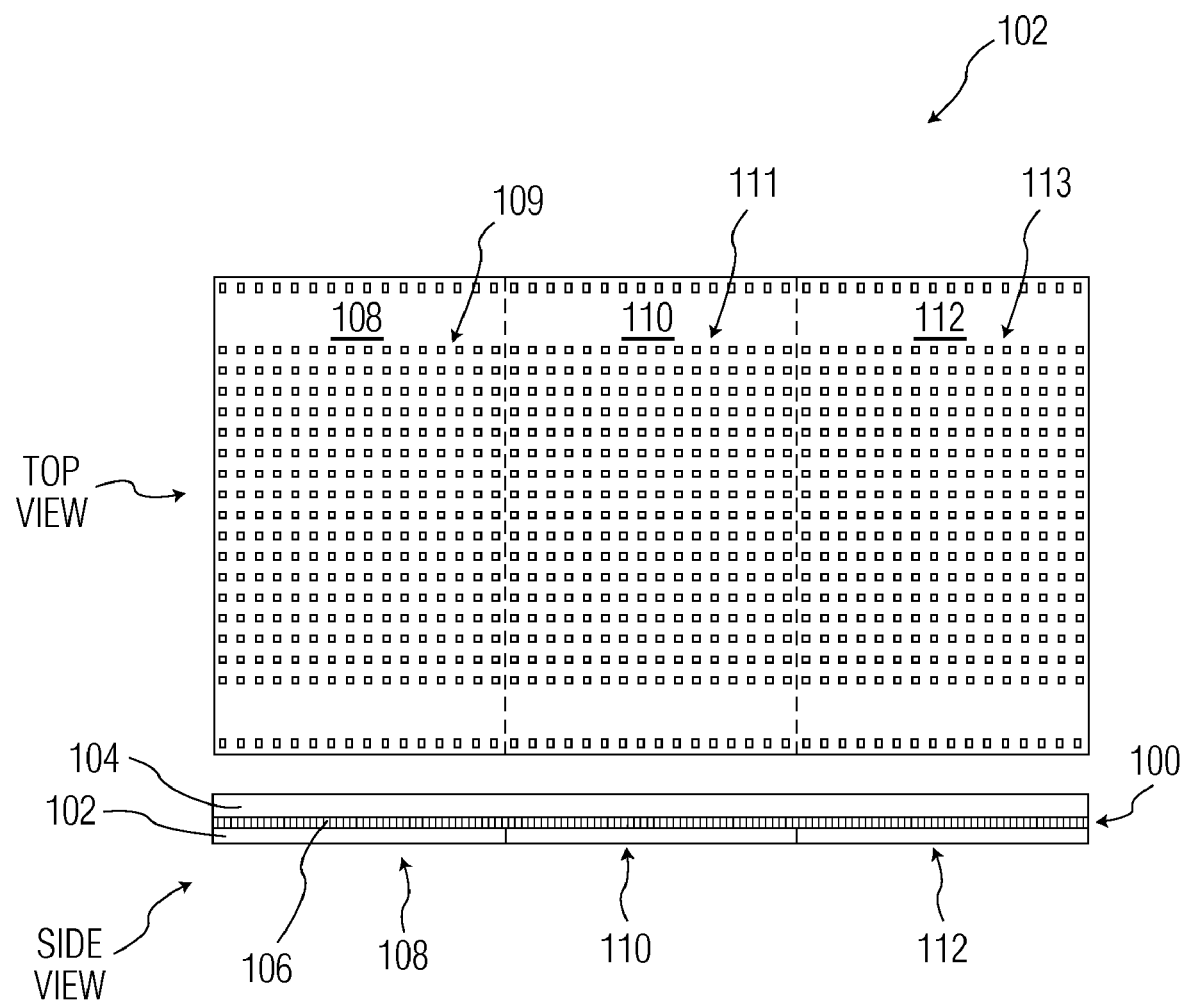
FIG. 8 is a top plan view of a portion of an ultrasound transducer in the formation of a large aperture array two dimensional ultrasound transducer using integrated circuits of FIG. 7 according to the yet another embodiment of the present disclosure.

FIG. 7 is a top plan view of a plurality of integrated circuit chips 90 on a wafer 92 for use in making large aperture array two dimensional ultrasound transducers according to yet another embodiment of the present disclosure. Desired ones of the integrated circuit chips 90 of wafer 92 are singulated along dicing lines indicated by reference numeral 94. FIG. 8 is a top plan view of a portion of an ultrasound transducer 100 in the formation of a large aperture array two dimensional ultrasound transducer using integrated circuits 90 of FIG. 7 according to the yet another embodiment of the present disclosure. The ultrasound transducer 100 comprises a combined individual die integrated circuit 102 and an array of acoustic elements (generally indicated by reference numeral 104) coupled to the combined individual die integrated circuit via an array of flip-chip bumps (generally indicated by reference numeral 106) and a suitable underfill material (not shown). The combined individual die integrated circuit 102 includes three individual integrated circuit die 90 aligned successively with respect to one other on a wafer 92. The three individual integrated circuit die 90 (corresponding to die 108, 110, and 112 of FIG. 8) are singulated together from the wafer 92 as the combined individual die integrated circuit 102. Furthermore, during a design portion of the particular ultrasound transducer application, individual die artwork on the wafer assures a continuation of an array pitch of the flip-chip bumps (generally indicated by reference numerals 109, 111 and 113, respectively) between adjacent die.

In yet another embodiment, the combined individual die integrated circuit further comprises a group of two or more individual die that have been singulated simultaneously from a wafer. Individual die artwork on the wafer assures a continuation of an array pitch of the flip-chip bumps between adjacent ones of the group of two or more individual die. Moreover, an array pitch of the flip-chip bumps is maintained substantially constant between adjacent ones of the group of two or more individual die.

Figure 9:
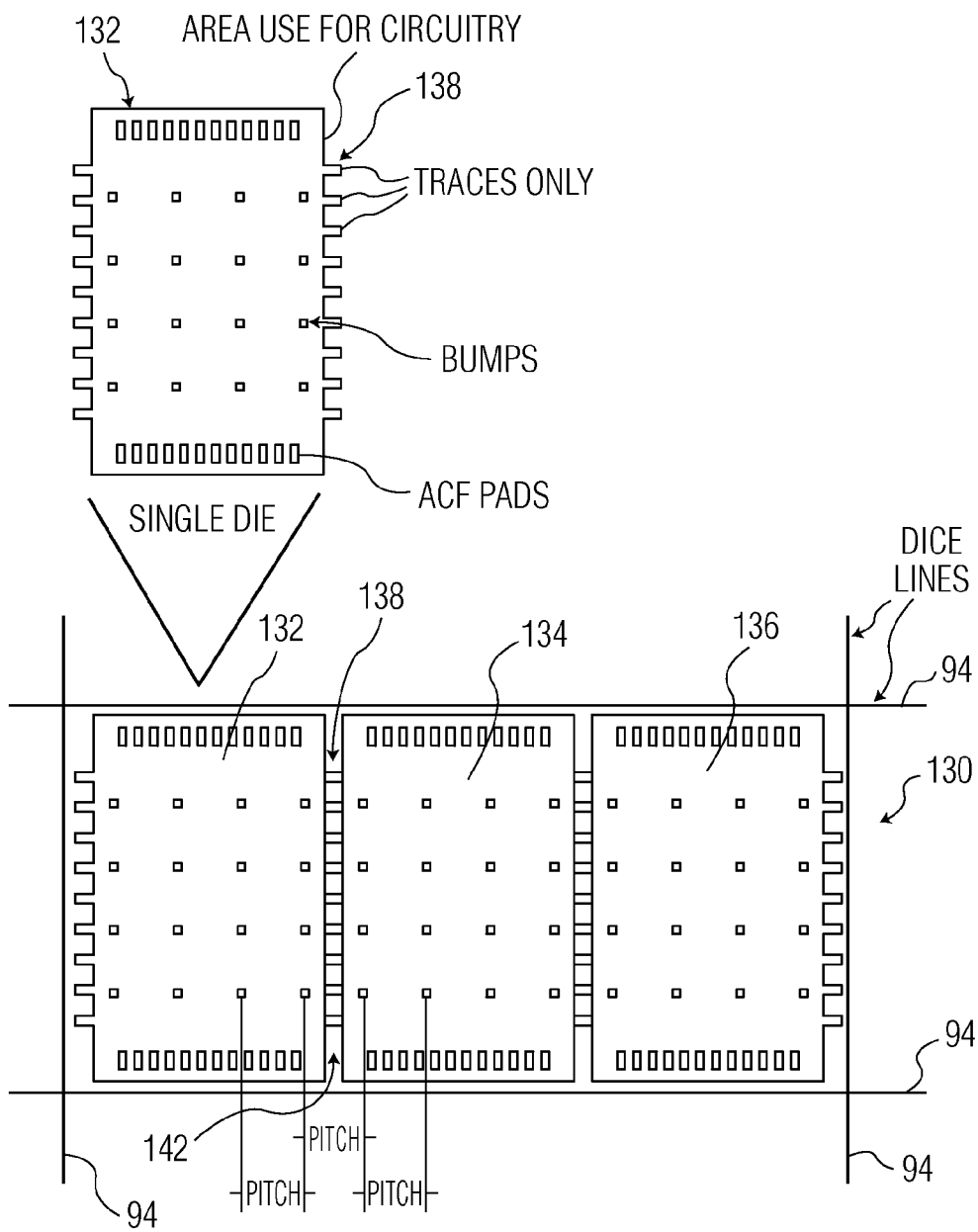
FIG. 9 is a top plan view of a portion of an ultrasound transducer in the formation of a large aperture array two dimensional ultrasound transducer according to another embodiment of the present disclosure.

FIG. 9 is a top plan view of a portion of an ultrasound transducer 120 in the formation of a large aperture array two dimensional ultrasound transducer according to another embodiment of the present disclosure. The first integrated circuit die and the at least one additional integrated circuit die can comprise two or more integrated circuit die (generally represented by reference numerals 132, 134, and 136). In this further embodiment, the first integrated circuit die 132 includes traces 138 along at least one side portion thereof. The at least one additional integrated circuit die 134 further includes traces 142 along at least one side portion thereof. Adjacent ones of a first integrated circuit die and an at least one additional integrated circuit die are stitched together at traces along adjacent side portions of adjacent one of the first and at least one additional integrated circuit die.

Figure 10:
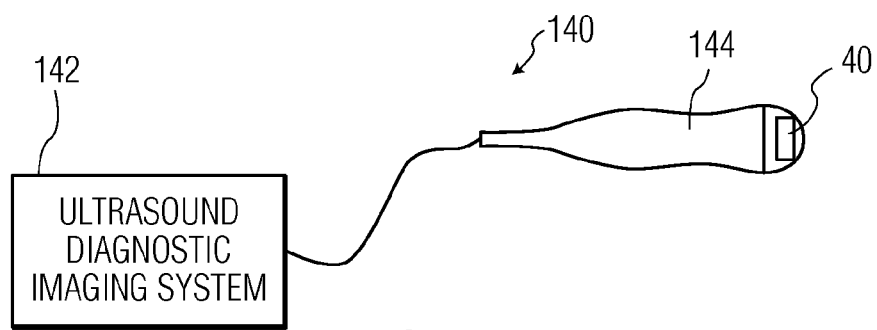
FIG. 10 is a block diagram view of an ultrasound diagnostic imaging system with an ultrasound transducer according to an embodiment of the present disclosure.

Referring now to FIG. 10, the figure illustrates a block diagram view of an ultrasound diagnostic imaging system 140 with an ultrasound transducer according to an embodiment of the present disclosure. Ultrasound diagnostic imaging system 140 includes a base unit 142 adapted for use with ultrasound transducer probe 144. Ultrasound transducer probe 144 includes ultrasound transducer 40 as discussed herein. Base unit 142 includes suitable electronics for performing ultrasound diagnostic imaging according to the requirements of a particular ultrasound diagnostic application. Ultrasound transducer probe 144 couples to base unit 142 via a suitable connection, for example, an electronic cable, a wireless connection, or other suitable means. Ultrasound diagnostic imaging system 140 can be used for performing various types of medical diagnostic ultrasound imaging. In addition, the ultrasound transducer of probe 144 can also include transducers 70, 100, and 130 as described and discussed herein.

Accordingly, an ultrasound diagnostic imaging system adapted for use with an ultrasound transducer 40 comprises a combined individual die integrated circuit and an array of acoustic elements coupled to the combined individual die integrated circuit via an array of flip-chip bumps. The combined individual die integrated circuit includes a first integrated circuit die aligned with at least one additional integrated circuit die. In addition, the first integrated circuit die, the second integrated circuit die integrated circuits, and the array of acoustic elements together form a large aperture two-dimensional transducer array.

A method of fabricating an ultrasound transducer comprises forming a combined individual die integrated circuit and coupling an array of acoustic elements to the combined individual die integrated circuit via an array of flip-chip bumps. The combined individual die integrated circuit includes a first integrated circuit die aligned with at least one additional integrated circuit die. The combined individual die integrated circuit further includes an array of flip chip bumps on flip-chip attachment surfaces of respective ones of the first integrated circuit die and the at least one additional integrated circuit die. Furthermore, the first integrated circuit die, the at least one additional integrated circuit die, and the array of acoustic elements together form a large aperture two-dimensional transducer array.

In another embodiment, the method further includes aligning the first integrated circuit die with the at least one additional integrated circuit die to preserve a continuation of the pitch between flip-chip bumps on the respective first and at least one additional integrated circuit die. The method can further include forming the combined individual die integrated circuit by mounting the first integrated circuit die and the at least one additional integrated circuit die on an alignment substrate.

In another embodiment, the method includes forming the combined individual die integrated circuit further by singulating individual ones of the first integrated circuit die and the at least one additional integrated circuit die from one or more wafers. In one instance, the first integrated circuit die and the at least one additional integrated circuit die comprise two individual singulated integrated circuit die, wherein the method further comprises aligning the two individual singulated integrated circuit die with respect to the other and mounting the aligned die on an alignment substrate.

In another embodiment, the combined individual die integrated circuit further comprises a group of two or more individual die that have been singulated simultaneously from a wafer. For example, the first integrated circuit die and the at least one additional integrated circuit die can comprise two individual integrated circuit die aligned with respect to the other on a wafer. Furthermore, the two individual integrated circuit die are singulated together from the wafer as the combined individual die integrated circuit. In another example, the first integrated circuit die and the at least one additional integrated circuit die can comprise three individual integrated circuit die aligned successively with respect to one other on a wafer. In the later instance, the three individual integrated circuit die are singulated together from the wafer as the combined individual die integrated circuit. Furthermore, individual die artwork on the wafer assures a continuation of an array pitch of the flip-chip bumps between adjacent die.

Accordingly, the embodiments of the present disclosure provide a path to implement flip-chip two dimensional technology to large size arrays, on the order of greater than 2 cm×2 cm. In one embodiment of the array fabrication process to achieve a large size IC, two or more of the individual ICs are positioned, aligned and attached to a flat substrate. The alignment of the individual dies includes preserving a continuation of the pitch between the pads on adjacent dies. After the alignment and attachment, a normal process of flip-chip can be performed.

In another embodiment of the present disclosure, the individual die artwork for a wafer is arranged in a way to assure continuation of the array pitch on adjacent dies. During a wafer die separation process, groups of two or more dies can be singulated together. Examplary applications for using the large size IC include a Large Footprint Abdominal Array, Linear Transducers and Large Curved Linear Arrays (CLA).

As disclosed herein, one solution for fabricating large IC size transducer arrays is to tile a number of smaller size dies next to each other. In addition, a stitching technique can be used to produce large size dies by connecting any number of adjacent dies. Connecting a number of adjacent dies is achieved by careful die design that purposely allow for dies to overlap during a step-and-repeat mask generation process. An advantage of such a stitching technique includes the requirement for a decreased number of connections required to a flex connector than would otherwise be required absent the stitching technique.

Typical die size is on the order of 15 mm high by 20 mm wide. With the embodiments of the present disclosure, a linear array could be formed using two die side by side to produce a 15 mm by 40 mm array. A 15 mm by 60 mm curved linear array could be formed using three die, as discussed herein with respect to the various embodiments. Although only a few exemplary embodiments have been described in detail above, those skilled in the art will readily appreciate that many modifications are possible in the exemplary embodiments without materially departing from the novel teachings and advantages of the embodiments of the present disclosure. For example, the array configurations disclosed herein could be modified to include one or more forms of a curved linear array (CLA). A curved linear array can be formed by bending the assembly to form a desired curvature of the curved linear array. In addition, the embodiments disclosed herein are not limited large aperture two dimensional arrays only, but could also be implemented for large aperture 1D and 1.5D arrays. 1D arrays include one row of transducer elements. 1.5D arrays include several rows of transducer elements, wherein the pitch between rows is larger than the pitch within a row. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The invention claimed is:

1. An ultrasound transducer, comprising:
   a combined individual die integrated circuit, the combined individual die integrated circuit including a first integrated circuit die aligned with at least one additional integrated circuit die; and
   an array of acoustic elements coupled to the combined individual die integrated circuit via an array of flip-chip bumps, wherein the first integrated circuit die, the at least one additional integrated circuit die, and the array of acoustic elements together form a large aperture transducer array,
   wherein the first integrated circuit die and the at least one additional integrated circuit die comprise two individual singulated integrated circuit dies.

2. The ultrasound transducer of claim 1, wherein the first integrated circuit die and the at least one additional integrated circuit die each comprise bond pads on a flip-chip attachment surface of a respective integrated circuit die, the bond pads having a pitch between adjacent bond pads.

3. The ultrasound transducer of claim 2, further wherein an alignment of the first integrated circuit die with the at least one additional integrated circuit die preserves a continuation of the pitch between bond pads on the respective first and at least one additional integrated circuit die.

4. The ultrasound transducer of claim 1, wherein the combined individual die integrated circuit further comprises the first integrated circuit die and the at least one additional integrated circuit die mounted on an alignment substrate.

5. The ultrasound transducer of claim 4, wherein the first integrated circuit die and the at least one additional integrated circuit die comprise two integrated circuit die.

6. The ultrasound transducer of claim 4, wherein the first integrated circuit die and the at least one additional integrated circuit die comprise three integrated circuit die.

7. The ultrasound transducer of claim 1, further wherein the two individual singulated integrated circuit die are aligned with respect to each other and mounted on an alignment substrate.

8. An ultrasound transducer, comprising:
   a combined individual die integrated circuit, the combined individual die integrated circuit including a first integrated circuit die aligned with at least one additional integrated circuit die; and
   an array of acoustic elements coupled to the combined individual die integrated circuit via an array of flip-chip bumps, wherein the first integrated circuit die, the at least one additional integrated circuit die, and the array of acoustic elements together form a large aperture transducer array, wherein the first integrated circuit die and the at least one additional integrated circuit die comprise two individual integrated circuit dies aligned with respect to the other on a wafer.

9. The ultrasound transducer of claim 8, further wherein the two individual integrated circuit die are singulated together from the wafer as the combined individual die integrated circuit.

10. The ultrasound transducer of claim 9, further wherein individual die artwork on the wafer assures a continuation of an array pitch of the flip-chip bumps between adjacent die.

11. An ultrasound transducer, comprising:
    a combined individual die integrated circuit, the combined individual die integrated circuit including a first integrated circuit die aligned with at least one additional integrated circuit die; and
    an array of acoustic elements coupled to the combined individual die integrated circuit via an array of flip-chip bumps, wherein the first integrated circuit die, the at least one additional integrated circuit die, and the array of acoustic elements together form a large aperture transducer array, wherein the first integrated circuit die and the at least one additional integrated circuit die comprise three individual integrated circuit dies aligned successively with respect to one other on a wafer.

12. The ultrasound transducer of claim 11, further wherein the three individual integrated circuit die are singulated together from the wafer as the combined individual die integrated circuit.

13. The ultrasound transducer of claim 12, further wherein individual die artwork on the wafer assures a continuation of an array pitch of the flip-chip bumps between adjacent die.

14. An ultrasound transducer, comprising:
    a combined individual die integrated circuit, the combined individual die integrated circuit including a first integrated circuit die aligned with at least one additional integrated circuit die; and
    an array of acoustic elements coupled to the combined individual die integrated circuit via an array of flip-chip bumps, wherein the first integrated circuit die, the at least one additional integrated circuit die, and the array of acoustic elements together form a large aperture transducer array, wherein the combined individual die integrated circuit further comprises a group of two or more individual die that have been singulated simultaneously from a wafer.

15. The ultrasound transducer of claim 14, further wherein individual die artwork on the wafer assures a continuation of an array pitch of the flip-chip bumps between adjacent ones of the group of two or more individual die.

* * * * *